US007968335B2

(12) United States Patent
Nakata

(10) Patent No.: US 7,968,335 B2
(45) Date of Patent: Jun. 28, 2011

(54) CELL CULTURING METHOD USING BIOMECHANICAL STIMULATION LOADING AND SYSTEM THEREFOR

(76) Inventor: Ken Nakata, Nishinomiya (JP)

(*) Notice: Subject to any disclaimer, the term of this patent is extended or adjusted under 35 U.S.C. 154(b) by 724 days.

(21) Appl. No.: 11/629,619

(22) PCT Filed: Jun. 16, 2005

(86) PCT No.: PCT/JP2005/011045
§ 371 (c)(1),
(2), (4) Date: Dec. 15, 2006

(87) PCT Pub. No.: WO2005/123905
PCT Pub. Date: Dec. 29, 2005

(65) Prior Publication Data
US 2008/0026465 A1    Jan. 31, 2008

(30) Foreign Application Priority Data

Jun. 17, 2004   (JP) .................................. 2004-209255

(51) Int. Cl.
*C12N 5/00* (2006.01)
(52) U.S. Cl. ............................ 435/325; 435/177; 600/36
(58) Field of Classification Search .................... 73/790, 73/807, 814, 818; 600/36, 57; 623/1.47, 623/13.17; 435/177, 325
See application file for complete search history.

(56) References Cited

U.S. PATENT DOCUMENTS

| 5,007,934 | A | * | 4/1991 | Stone .......................... 623/14.12 |
| 5,622,819 | A | | 4/1997 | Herman |
| 5,882,929 | A | | 3/1999 | Fofonoff et al. |
| 6,287,340 | B1 | * | 9/2001 | Altman et al. ............. 623/13.11 |
| 2004/0147015 | A1 | | 7/2004 | El-Haj et al. |

FOREIGN PATENT DOCUMENTS

| JP | 11-502715 | 3/1999 |
| JP | 2002-510482 | 4/2002 |
| JP | 2003-265164 | 9/2003 |
| JP | 2004-113222 | 4/2004 |
| WO | 02/051985 | 7/2002 |

* cited by examiner

*Primary Examiner* — Michael A Marcheschi
*Assistant Examiner* — Michael Hobbs
(74) *Attorney, Agent, or Firm* — Wenderoth, Lind & Ponack L.L.P.

(57) ABSTRACT

A cell culturing method employing biomechanical stimulation loading and a system for applying, in in vitro culture, stimulation similar to vertical weight load stimulation or sideward shear stress stimulation acting on tissues in an aboveground living body as repeated biomechanical stimulation to culture cells, culture tissues or a construct including the culture cells. The system includes a mechanical stimulation loading device and a culture receptacle that are placed in a carbon dioxide incubator, and a control computer. The device includes a weight loading piston, a piston raising and lowering stage supporting piston to allow vertical movement of a piston within a designated range, and a stage lifting and lowering mechanism for vertically moving the stage. A computer drives the mechanism in a specified cycle to effect the vertical movement of the stage. When the stage is lowered, a culture in the receptacle is weighted with the piston.

9 Claims, 7 Drawing Sheets

F I G. 1
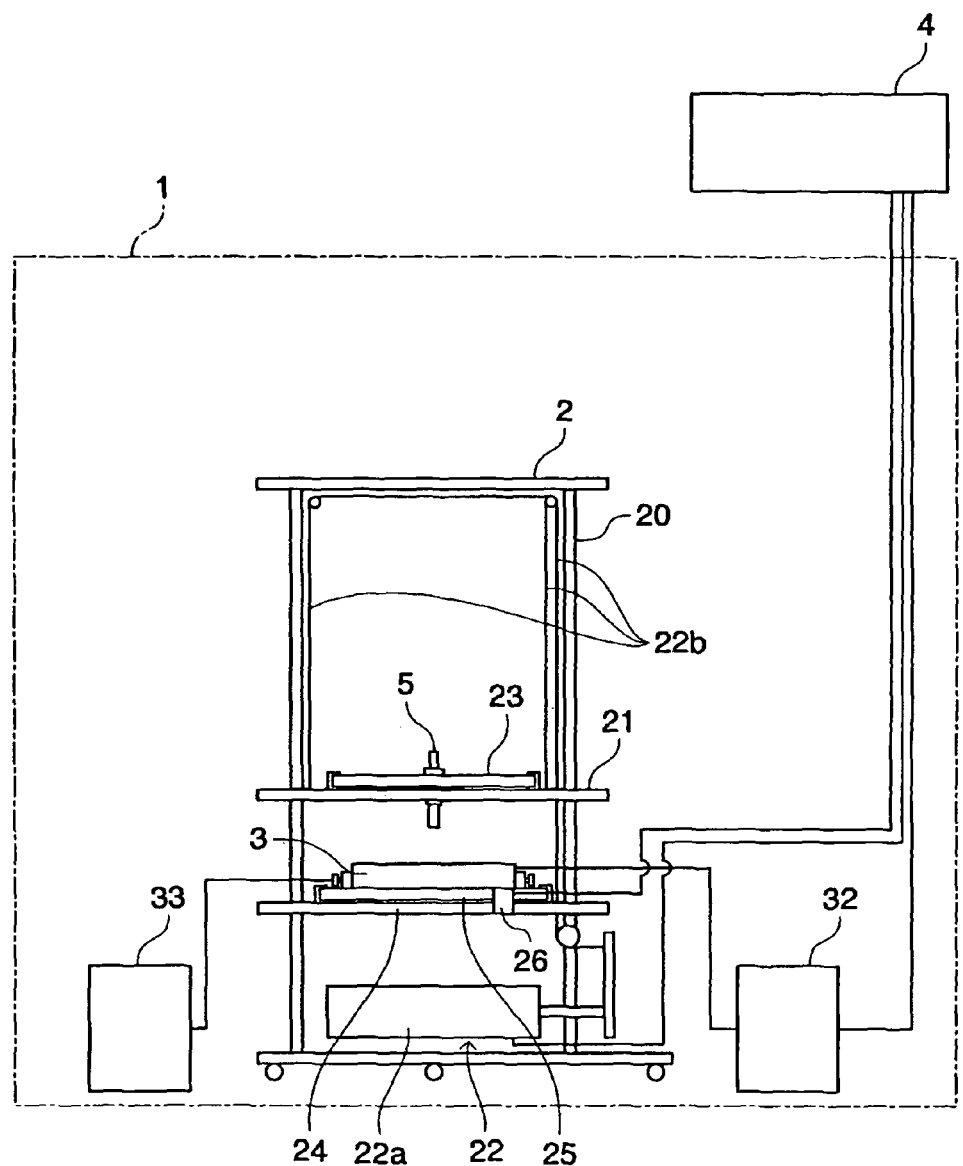

F I G. 2
(a)
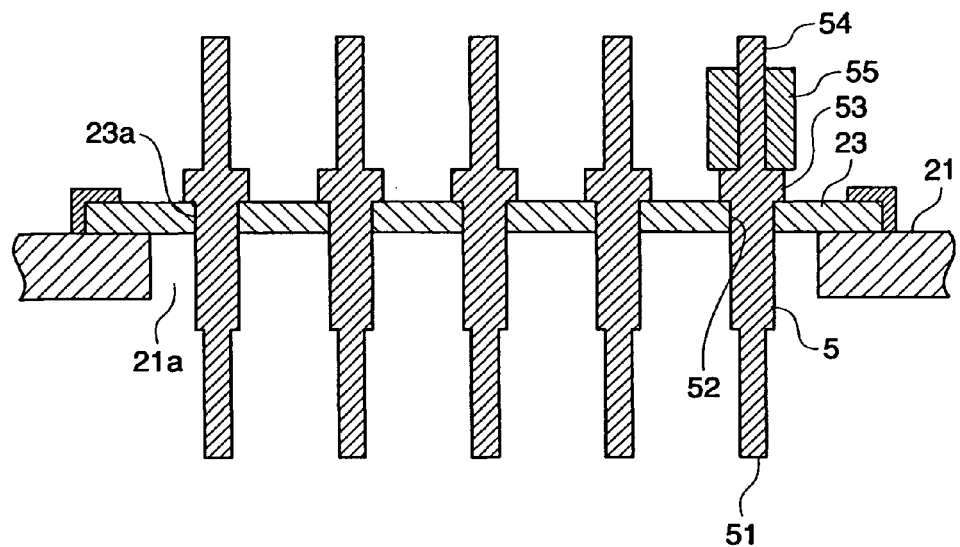
(b)
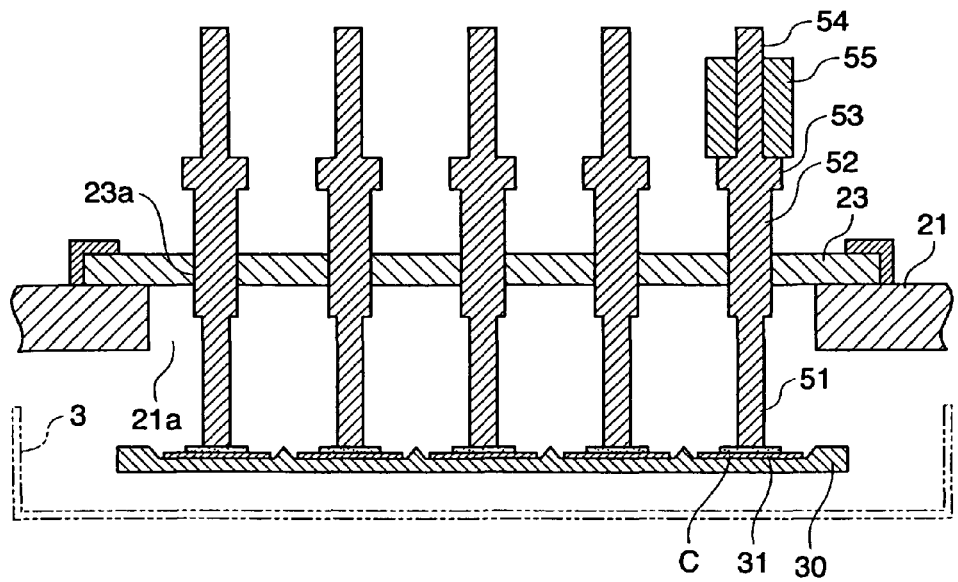

F I G. 6
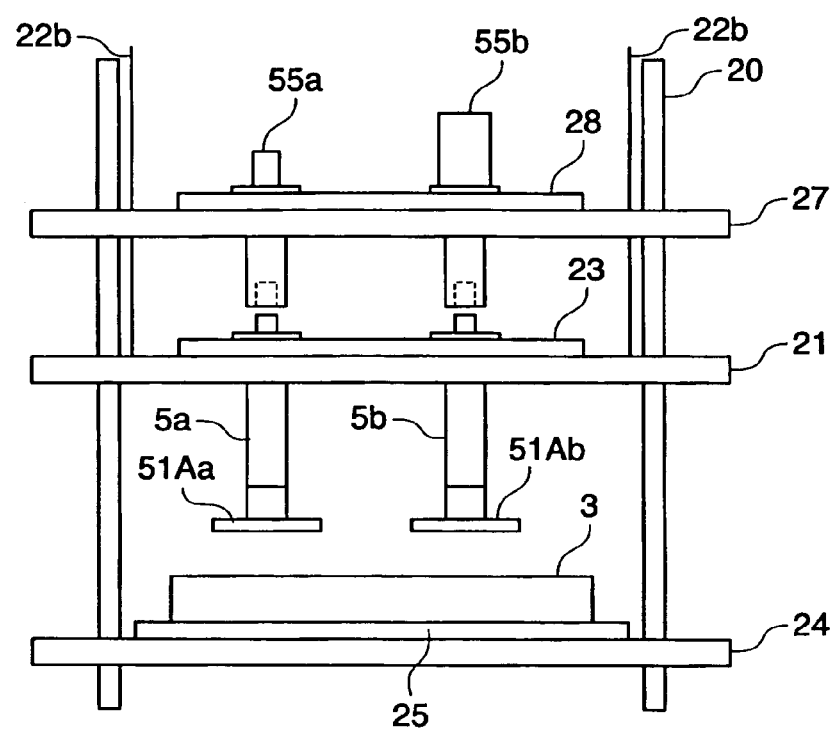

CELL CULTURING METHOD USING BIOMECHANICAL STIMULATION LOADING AND SYSTEM THEREFOR

BACKGROUND OF THE INVENTION

I. Technical Field

The present invention relates to a cell culturing method employing biomechanical stimulation loading and its system for applying, in in vitro culture, repeated biomechanical stimulation to culture cells, culture tissues and a construct including the culture cells (which are collectively referred to as "cultures" in the description). The repeated biomechanical stimulation is stimulation similar to vertical weight load stimulation or sideward shear stress stimulation which acts on tissues in an aboveground living body.

II. Description of the Related Art

As an approach to treating patients with cartilage lesions, cell transplantation therapy has been recently carried out, for example, in Europe and America. In this approach, remaining healthy cartilage tissues are taken out from the patients, cartilage cells are separated from the tissues and undergo in vitro culture for growth, and cultured cartilage cells are transplanted back to the patients.

This approach, which carries out the in vitro cartilage cell culture and growth, however has problems that it does not carry out in vitro regeneration of cartilage tissues, produces an unstable effect and requires long-term repair and maturation of the cartilage tissues.

In the living body, tissues and cells are subjected to not only biochemical stimulation but also mechanical stimulation attributed to gravity, muscle contraction force or external force. Culture cells and culture tissues are known to change their functions including growth, differentiation and metabolism by experiencing biomechanical stimulation in static or dynamic form.

Based on such findings, cell and tissue culture systems utilizing the biomechanical stimulation have been recently studied and put to practical use by several domestic and foreign research groups, including, for example, a system disclosed in Japanese Patent Unexamined Publication No. 2003-265164.

Culture systems using stress stimulation include a method of expanding and contracting or shaking a membrane member to which the cells are adhered for culturing the cartilage cells or vascular smooth muscle cells, and a method of placing a support holding the cartilage cells in a column and applying the stress stimulation to the cartilage cells held by the support by means of the flow of culture medium or culture fluid circulated by a pump for culturing the cartilage cells.

Culture systems using hydrostatic pressure stimulation include a method of applying pressure to the cartilage cells by means of a gas cylinder for stimulation loading and a method of pressurizing the column with a 5 MPa load, which is equivalent to intra-articular pressure, by means of a hydraulic cylinder pump for stimulating the cartilage cells.

There has also been proposed a cell culture system in which the culture medium is fed into the column (that is, to a device in the column) by a pump and the flow rate of the culture medium is varied by operation of a valve or the like for desired pressure loading patterns and cycles.

These methods and systems re-create conditions close to those in the living body, such as levels of pressure on the cells in the living body, pressure variations and patterns in pressure rise and drop, through use of the culture fluid. However, these methods and systems are strictly for the purpose of stimulating the culture cells by expanding the culture cells and using the flow of culture fluid and the culture fluid, not re-creating vertical biomechanical stimulation, which is attributed to gravity, to support tissues of a bone, a cartilage or the like.

As is obvious from the known fact that healthy astronauts who experience reduced gravity stimulation in outer space of microgravity and patients and aged persons who have to stay on beds develop osteoporosis at their spines, arms and legs, the vertical repeated stimulation attributed to gravity is of importance to the living body.

SUMMARY OF THE INVENTION

As described above, the prior arts do not re-create the vertical weight load stimulation attributed to gravity to the culture cells and also force on the cells surrounded by an extracellular tissue matrix.

It is an object of the present invention to provide a cell culturing method employing biomechanical stimulation loading and its system for applying, in in vitro culture, repeated biomechanical stimulation to culture cells, culture tissues or a construct including the culture cells. The repeated biomechanical stimulation is stimulation similar to vertical weight load stimulation or sideward shear stress stimulation acting on tissues in an aboveground living body.

To achieve the above object, a cell culturing method employing biomechanical stimulation loading according to the present invention is a method of applying a biomechanical stimulation to a culture in a culture receptacle placed in a carbon dioxide incubator, wherein a vertical weight load stimulation of the biomechanical stimulations is applied to the culture in the culture receptacle by weighting the culture in the culture receptacle with a weight loading piston in a specified cycle.

In this case, a sideward shear stress stimulation of the biomechanical stimulations can be applied to the culture by moving or shaking the culture receptacle containing the culture on a horizontal plane, while the vertical weight load stimulation is applied to the culture in the culture receptacle.

A biomechanical stimulation loading system for carrying out the invention's above-described cell culturing method employing the biomechanical stimulation loading includes: a mechanical stimulation loading device; a culture receptacle; and a control computer, the mechanical stimulation loading device and the culture receptacle being placed in a carbon dioxide incubator, wherein the mechanical stimulation loading device includes: a weight loading piston; a piston raising and lowering stage supporting the weight loading piston to allow vertical movement of the weight loading piston within a designated range; and a stage lifting and lowering mechanism for vertically moving the piston raising and lowering stage, wherein the control computer drives the stage lifting and lowering mechanism in a specified cycle to effect the vertical movement of the piston raising and lowering stage, and wherein a culture in the culture receptacle is weighted with the weight loading piston when the piston raising and lowering stage is lowered.

In this case, the weight loading piston can be mounted with an additional load weight at its upper end part.

The weight loading piston can be mounted with, at its lower end part, a pressure member having a shape suitable for the culture.

The piston raising and lowering stage can support the plurality of weight loading pistons.

The piston raising and lowering stage can support the weight loading pistons via a piston mounting stage mounted above the piston raising and lowering stage.

The piston mounting stage supporting the weight loading pistons can be movable on a horizontal plane in relation to the piston raising and lowering stage.

The weight loading pistons can be supported by one of the piston raising and lowering stage and the piston mounting stage to be prevented from rotating during the vertical movement.

The culture receptacle can be detachably mounted to a culture receptacle holding stage of the mechanical stimulation loading device.

A shear stress loading mechanism can be provided for moving or shaking the culture receptacle on a horizontal plane.

The culture receptacle can accommodate a fixable receptor having a predetermined shape, and a weight load stimulation part for the culture can be defined by the pressure member provided at the lower end part of the weight loading piston and the receptor to be similar to a given shape of one of parts including a knee joint.

The weight load stimulation part defined by the pressure member provided at the lower end part of the weight loading piston and the receptor can be provided with a member made of a biocompatible synthetic resin material.

According to the invention's cell culturing method employing the biomechanical stimulation loading, the culture in the culture receptacle experiences the vertical weight load stimulation by being weighted with the weight loading piston in the specified cycle. In this way, the culture can be subjected to the stimulation similar to vertical weight load stimulation acting on tissues in an aboveground living body and can be cultured in a state closely mimicking an in vivo tissue environment. This enables production of differentiated and maturated cultures capable of withstanding a mechanical load after transplantation and efficient repair and maturation of the biological tissues.

While the vertical weight load stimulation is applied to the culture in the culture receptacle, moving or shaking the culture receptacle containing the culture on the horizontal plane effects application of the sideward shear stress stimulation. In this way, the culture can be subjected to the stimulation similar to sideward shear stress stimulation acting on the tissues in the aboveground living body and can be cultured in a state closely mimicking an in vivo tissue environment. This enables production of differentiated and maturated cultures capable of withstanding a mechanical load after transplantation and more efficient repair and maturation of the biological tissues.

According to the invention's biomechanical stimulation loading system for carrying out the above-mentioned cell culturing method employing the biomechanical stimulation loading, the mechanical stimulation loading device includes the weight loading piston, the piston raising and lowering stage supporting the weight loading piston to allow the vertical movement of the weight loading piston within the designated range and the stage lifting and lowering mechanism for vertically moving the piston raising and lowering stage, the control computer drives the stage lifting and lowering mechanism in the specified cycle to effect the vertical movement of the piston raising and lowering stage, and the culture in the culture receptacle is weighted with the weight loading piston when the piston raising and lowering stage is lowered. Such a system of applying the stimulation similar to the vertical weight load stimulation acting on the tissues in the aboveground living body to the culture with accuracy can thus be readily made at low cost.

Mounting the additional load weight to the upper end part of the weight loading piston allows a precise and easy adjustment to the magnitude of vertical weight load stimulation applied to the culture.

Mounting the pressure member having the shape suitable for the culture to the lower end part of the weight loading piston allows accurate application of the stimulation similar to the vertical weight load stimulation acting on the tissues in the aboveground living body to the culture.

With the piston raising and lowering stage supporting the plurality of weight loading pistons, the plurality of cultures can be subjected simultaneously to vertical weight load stimulations of the same magnitude or of different magnitudes, for efficient culture.

With the piston raising and lowering stage supporting the weight loading pistons via the piston mounting stage mounted above the piston raising and lowering stage, support for the weight loading pistons of various kinds can be facilitated.

With the piston mounting stage, which support the weight loading pistons, being movable on the horizontal plane in relation to the piston raising and lowering stage, different vertical weight load stimulations can be applied to the same culture.

Having the weight loading pistons supported by the piston raising and lowering stage or the piston mounting stage to prevent rotation of the weight loading pistons during their vertical movement allows accurate application of the stimulation similar to the vertical weight load stimulation acting on the tissues in the aboveground living body to the culture even when the pressure member having the shape suitable for the culture is mounted to the lower end part of each of the weight loading pistons.

Detachably mounting the culture receptacle to the culture receptacle holding stage of the mechanical stimulation loading device facilitates placement of culture receptacles of various kinds.

With the shear stress loading mechanism which moves or shakes the culture receptacle on the horizontal plane provided, the system that applies the stimulation similar to the sideward shear stress stimulation acting on the tissues in the aboveground living body to the culture with accuracy can be readily made at low cost.

Placing the fixable receptor having the predetermined shape in the culture receptacle and defining the weight load stimulation part for the culture by means of the pressure member provided at the lower end part of the weight loading piston and the receptor so that the weight load stimulation part will be similar to the given shape of one of the parts including the knee joint facilitate re-creation of force on cells surrounded by an extracellular tissue matrix.

Providing the member made of the biocompatible synthetic resin material to the weight load stimulation part defined by the pressure member provided at the lower end part of the weight loading piston and the receptor enables the culture to be cultured in a state closely mimicking an in vivo tissue environment, thereby improving biocompatibility of the culture after transplantation.

BRIEF DESCRIPTION OF THE DRAWINGS

FIG. 1 is a general view of a biomechanical stimulation loading system in accordance with a first exemplary embodiment of the present invention.

FIG. 2 shows an essential part of the first embodiment.

FIG. 6 illustrates an essential part of the second embodiment.

DETAILED DESCRIPTION OF THE INVENTION

Figure 3:
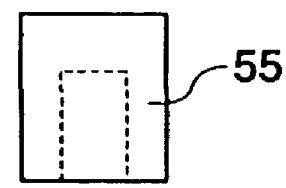
FIG. 3 is an exploded view of a weight loading piston.
Figure 3:
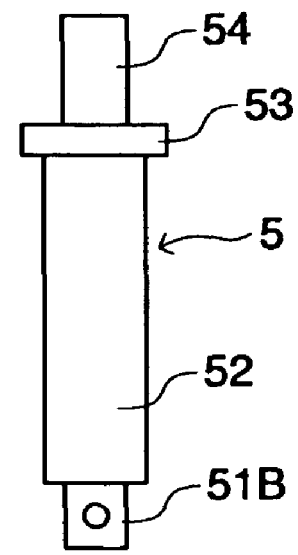
Figure 3:
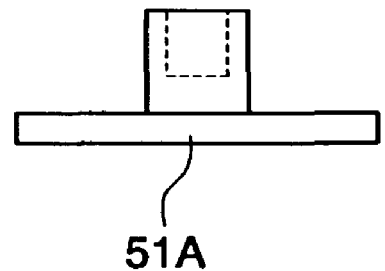

Exemplary embodiments of a cell culturing method employing biomechanical stimulation loading and its system according to the present invention are demonstrated hereinafter with reference to the accompanying drawings.

First Exemplary Embodiment

FIGS. 1 and 2 illustrate a biomechanical stimulation loading system for carrying out the invention's cell culturing method employing the biomechanical stimulation loading in accordance with the first exemplary embodiment.

This biomechanical stimulation loading system is comprised of mechanical stimulation loading device 2 and culture receptacle 3 that are placed in carbon dioxide incubator 1, and control computer 4.

Operations of the biomechanical stimulation loading system are all effected from outside carbon dioxide incubator 2, thereby permitting long-duration culture with the interior of incubator 2 kept sterilized.

The interior of carbon dioxide incubator 2 is used in a sterilized environment in which temperature, humidity, partial pressures of oxygen, carbon dioxide and nitrogen and others are controlled.

Mechanical stimulation loading device 2 installed in this carbon dioxide incubator 1 includes weight loading pistons 5, piston raising and lowering stage 21 supporting weight loading pistons 5 to allow vertical movement of pistons 5 within a designated range, and stage lifting and lowering mechanism 22 for vertically moving piston raising and lowering stage 21. Stage lifting and lowering mechanism 22 is driven by control computer 4 in a specified cycle for vertically moving piston raising and lowering stage 21. When piston raising and lowering stage 21 is lowered, culture C in culture receptacle 3 is weighted with corresponding weight loading piston 5.

This structure allows application of stimulation which is similar to vertical weight load stimulation acting on tissues in an aboveground living body to culture C.

Stage lifting and lowering mechanism 22 for vertically moving piston raising and lowering stage 21 is composed of, for example, electric actuator 22a and wire 22b, connected to electric actuator 22a, and with which piston raising and lowering stage 21 is suspended.

Control computer 4 issues a command to operate electric actuator 22a, whereby piston raising and lowering stage 21 can move vertically along guide member 20 with the aid of wire 22b.

In the present embodiment, piston raising and lowering stage 21 supports the plurality of (for example, a total of twenty five made by five times five) weight loading pistons 5 via piston mounting stage 23 mounted on piston raising and lowering stage 21.

Piston raising and lowering stage 21 in this case is intended for placement of piston mounting stage 23 thereon and is thus formed with opening 21a at its center to permit free vertical movement of weight loading pistons 5.

In this way, support for weight loading pistons 5 of various kinds can be facilitated.

It is to be noted that piston raising and lowering stage 21 can support weight loading pistons 5 directly without the use of piston mounting stage 23.

Each weight loading piston 5 is formed with pressure member 51, which has a shape suitable for culture C, at its lower end part, guide shank 52, which is fit through hole 23a formed in piston mounting stage 23, at its intermediate part, large-diameter part 53 positioned above guide shank 52, and weight mounting part 54 at its upper end part to which additional load weight 55 is mounted.

As shown in FIG. 2(a), piston raising and lowering stage 21 is moved down with weight loading pistons 5 supported by piston mounting stage 23. When piston raising and lowering stage 21 is lowered, respective large-diameter parts 53 of weight loading pistons 5 are released from the support by piston mounting stage 23 as shown in FIG. 2(b), whereby culture C in culture receptacle 3 is directly weighted with corresponding weight loading piston 5.

Thereafter, piston raising and lowering stage 21 is moved up for returning weight loading pistons 5 to the state of FIG. 2(a) in which pistons 5 are supported by piston mounting stage 23.

A vertical weight load stimulation loading cycle of weight loading pistons 5 and a period of time during which the vertical weight load stimulation is loaded by piston 5 can be controlled freely by operation of control computer 4.

Additional load weight 55 can be mounted to weight mounting part 54 on an as needed basis and can be freely adjusted in weight, so that an easy adjustment can be made to the magnitude of vertical weight load stimulation applied to culture C.

Pressure member 51 of weight loading piston 5 can have the desired shape suitable for culture C. As shown in FIG. 3 illustrating a modification of weight loading piston 5, pressure member 51A having a shape suitable for culture C can be formed as a discrete member for attachment to lower end part 51B of weight loading piston 5.

Accordingly, the stimulation similar to the vertical weight load stimulation acting on the tissues in the aboveground living body can be applied to culture C with accuracy.

Weight loading pistons 5 can be supported by piston mounting stage 23 (or piston raising and lowering stage 21) to be prevented from rotating during their vertical movement.

Specifically, holes 23a in piston mounting stage 23 are made polygonal, and guide shank 52 is formed to have a polygonal cross section fitting corresponding polygonal hole 23a.

Consequently, the stimulation similar to the vertical weight load stimulation acting on the tissues in the aboveground living body can be applied to culture C with accuracy even in cases where pressure member 51A having the shape (any shape but a circular shape) suitable for culture C is mounted to lower end part 51B of weight loading piston 5.

Culture receptacle 3 is detachably mounted to culture receptacle holding stage 24 of mechanical stimulation loading device 2.

This facilitates placement of culture receptacles 3 of various kinds.

Culture receptacle 3 can be connected to culture medium tank (for injection) 32 and culture medium tank (for discharge) 33 on an as needed basis, and injection and discharge of culture medium can be controlled by control computer 4.

Shear stress loading mechanism 26 is provided for moving or shaking culture receptacle 3 on a horizontal plane.

Specifically, shear stress stage 25 is disposed above culture receptacle holding stage 24 so as to be movable on the horizontal plane in relation to culture receptacle holding stage 24, culture receptacle 3 is mounted on this shear stress stage 25, and shear stress stage 25 is moved or shaken on the horizontal plane by shear stress loading mechanism 26.

Moving or shaking on the horizontal plane can be in a desired direction or directions. For example, moving or shaking on the horizontal plane can be in one direction, in X and Y directions or along a circle.

Examples that find use as shear stress loading mechanism 26 can include an electric actuator and a moving or shaking mechanism which is a combination of a permanent magnet and an electromagnet. This shear stress loading mechanism 26 is driven by control computer 4.

In this way, stimulation similar to such sideward shear stress stimulation acting on the tissues in the aboveground living body as stimulation acting on a knee joint during bending and stretching exercises can be applied to culture C.

It is to be noted here that diagonal shear stress stimulation can also be applied by moving or shaking culture receptacle 3 on the horizontal plane by means of shear stress loading mechanism 26 while adjusting the application of vertical weight load stimulation using weight loading piston 5 to culture C in culture receptacle 3

Figure 4:
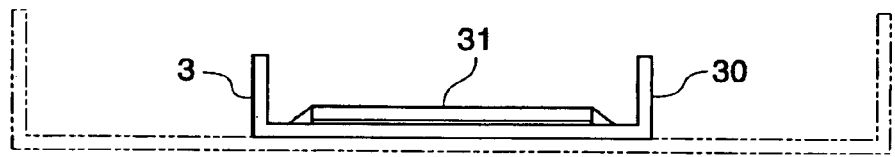
FIG. 4 illustrates an internal culture receptacle and a receptor.

Placed in culture receptacle 3 is internal culture receptacle 30 having a desired shape suitable for cultures C as shown in FIGS. 2(b) and 4. This internal culture receptacle 30 accommodates, in each position facing pressure member 51 of weight loading piston 5, receptor 31 consisting of culture cells, culture tissues or a construct including the culture cells, and culture C consisting of culture cells, culture tissues or a construct including the culture cells is placed above this receptor 31.

Pressure member 51A of weight loading piston 5 shown in FIG. 3 and flat receptor 31 of internal culture receptacle 30 shown in FIG. 4 are suitable for such culture C as dermal culture tissues and thus allow application of the vertical weight load stimulation as well as the sideward shear stress stimulation to the dermal culture tissues.

Second Exemplary Embodiment

Figure 5:
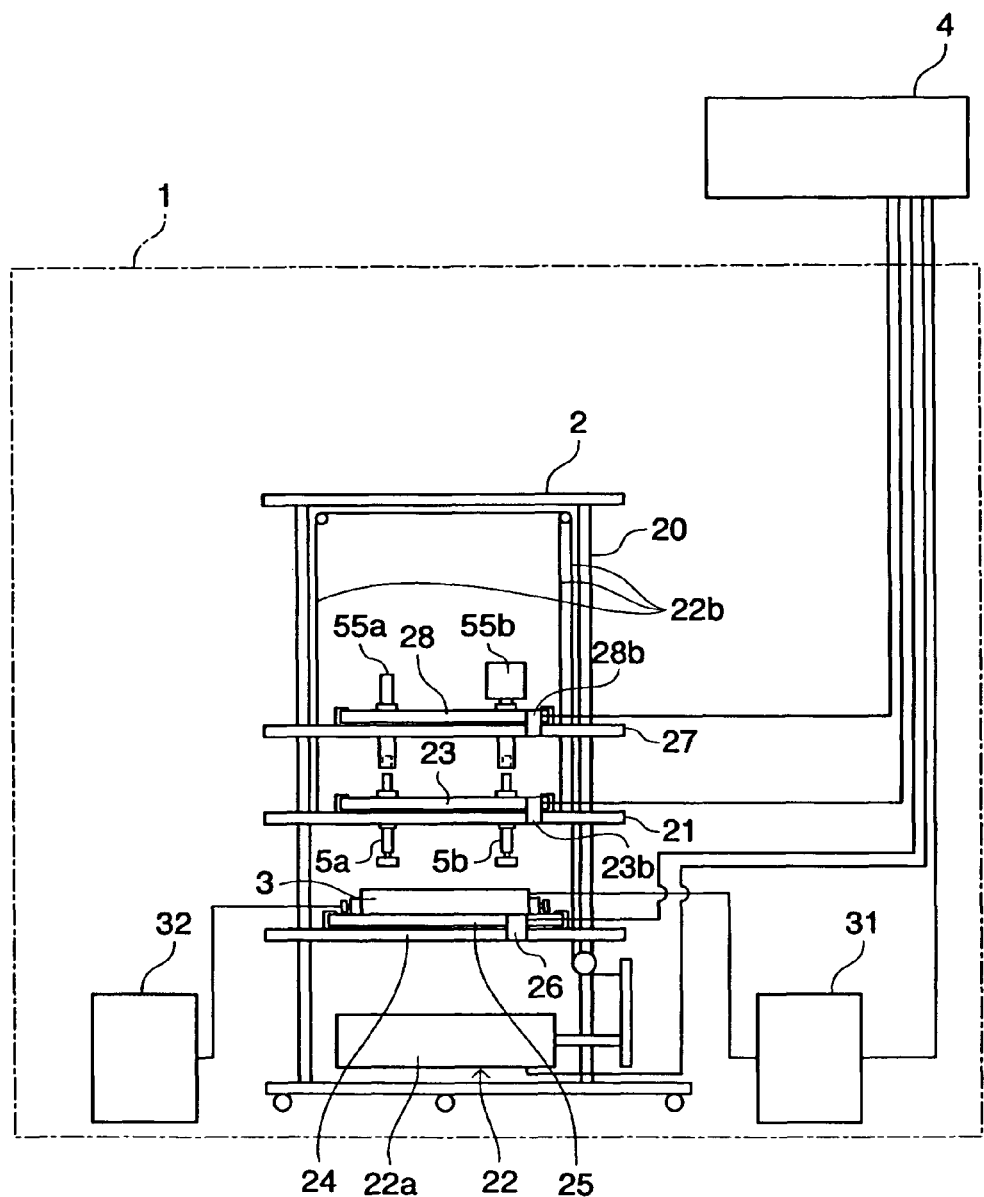
FIG. 5 is a general view of a biomechanical stimulation loading system in accordance with a second exemplary embodiment of the invention.

FIGS. 5 and 6 illustrate a biomechanical stimulation loading system for carrying out the invention's cell culturing method employing the biomechanical stimulation loading in accordance with the second exemplary embodiment.

This biomechanical stimulation loading system consists in the first embodiment's biomechanical stimulation loading system provided with additional features. Those additional features include having piston mounting stage 23, which supports a plurality of various weight loading pistons 5a, 5b (with respective pressure members 51Aa, 51Ab), movable on a horizontal plane in relation to piston raising and lowering stage 21, having additional load weight mounting stage 28, which supports a plurality of additional load weights 55a, 55b of various kinds, movable on a horizontal plane in relation to additional load weight raising and lowering stage 27 and allowing desired selections from combinations of weight loading pistons 5a, 5b and additional load weights 55a, 55b.

More specifically, piston mounting stage 23 is disposed above piston raising and lowering stage 21 so as to be movable (that is, for example, rotatable) on the horizontal plane in relation to piston raising and lowering stage 21, and additional load weight mounting stage 28 is similarly disposed above additional load weight raising and lowering stage 27 to be movable (that is, for example, rotatable) on the horizontal plane in relation to additional load weight raising and lowering stage 27. These piston mounting stage 23 and additional load weight mounting stage 28 are caused by piston mounting stage driving mechanism 23b and additional load weight mounting stage driving mechanism 28b, respectively, to move (that is, for example, to rotate) independently on their respective horizontal planes.

Examples that find use as piston mounting stage driving mechanism 23b and additional load weight mounting stage driving mechanism 28b can include a driving mechanism which is a combination of an electric motor and a gear. These driving mechanisms 23b and 28b are driven by control computer 4.

As shown in FIGS. 5 and 6, piston raising and lowering stage 21 and additional load weight mounting stage 28 are moved down with weight loading pistons 5a, 5b supported by piston mounting stage 23 and with additional load weights 55a, 55b supported by additional load weight mounting stage 28. When piston raising and lowering stage 21 and additional load weight mounting stage 28 are lowered, large-diameter parts 53 of weight loading pistons 5 and additional load weights 55a, 55b are released from the respective supports by piston mounting stage 23 and additional load weight mounting stage 28 in succession, whereby cultures C in culture receptacle 3 are directly weighted with corresponding weight loading pistons 5a, 5b and corresponding additional load weights 55a, 55b.

Thereafter, piston raising and lowering stage 21 and additional load weight mounting stage 28 are moved up for returning weight loading pistons 5a, 5b to a state of FIG. 2 or 6 in which these pistons 5a, 5b are supported by piston mounting stage 23 and for returning additional load weights 55a, 55b to a state of FIG. 6 in which these weights 55a, 55b are supported by additional load weight mounting stage 28.

With this structure, the desired selections can be made from the combinations of weight loading pistons 5a, 5b and additional load weights 55a, 55b, whereby vertical weight load stimulations of various magnitudes as a result of using different weight loading pistons 5a, 5b (with pressure members 51Aa, 51Ab) can be applied to the same culture C with ease.

The other components and functions of this embodiment's biomechanical stimulation loading system are similar to those of the biomechanical stimulation loading system of the first embodiment.

Third Exemplary Embodiment

Figure 7:
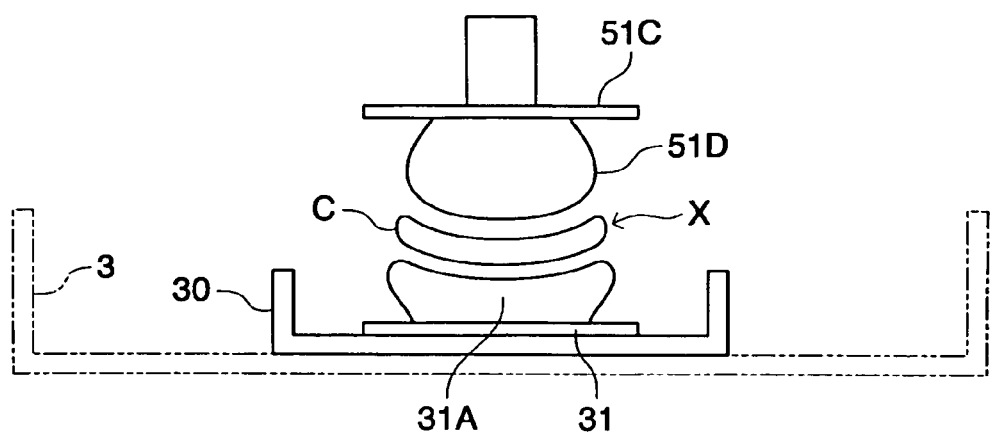
FIG. 7 shows an example of meniscus tissue culture by a biomechanical stimulation loading system in accordance with a third exemplary embodiment of the invention, illustrating an osteochondral structure of a knee joint.

FIG. 7 shows the third exemplary embodiment of a biomechanical stimulation loading system for carrying out the invention's cell culturing method employing the biomechanical stimulation loading.

This embodiment's biomechanical stimulation loading system is suitable for culturing, for example, a meniscus, an articular lip and an articular disc. Placed in culture receptacle 3 is internal culture receptacle 30 suitable for culture C. This internal culture receptacle 30 accommodates, in a position facing pressure member 51C of weight loading piston 5, receptor 31 consisting of culture cells, culture tissues or a construct including the culture cells, and culture C consisting of culture cells, culture tissues or a construct including the culture cells is placed above this receptor 31.

The meniscus, the articular lip, the articular disc and others undergo weight load stimulation in a living body not with a hardness similar to that of a bone but via bone-cartilage units. Accordingly, in culture (of, for example, the meniscus), artificial femoral bone-cartilage unit 51D, made of biocompatible synthetic resin, and which is similar to a femoral bone-cartilage unit, is mounted to pressure member 51C of weight loading piston 5, and artificial tibial bone-cartilage unit 31A, made of biocompatible synthetic resin, and which is similar to a tibial bone-cartilage unit is mounted on receptor 31, whereby weight load stimulation part X for the culture is defined between unit 51D and unit 31A to be similar to a given shape of the living body (that is, a knee joint in this case). Culture C (in a culture dish shaped specifically for the meniscus in this case) is then inserted into this weight load stimulation part X for re-creation of the weight load stimulation via the bone-cartilage units (at the knee joint in this case).

This facilitates re-creation of force on the cells surrounded by an extracellular tissue matrix and allows culture C to be cultured in a state closely mimicking an in vivo tissue environment, thereby improving biocompatibility of the culture after transplantation.

It is to be noted here that, culture C consisting of the culture tissues or the construct including the culture cells can be formed into a shape suitable for transplantation in advance. Specifically, a three-dimensional biomaterial-based cell support, such as a cell support mainly composed of collagen, is used as the matrix of the construct including the culture cells and is seeded with and bonded to cartilage cells or meniscus cells to form the construct including the culture cells.

The other components and functions of this embodiment's biomechanical stimulation loading system are similar to those of the biomechanical stimulation loading systems of the first and second embodiments.

The present invention can perform on the culture consisting of the culture cells, the culture tissues or the construct including the culture cells the direct biomechanical stimulation loading by utilizing gravity for the vertical weight load stimulation and moving or shaking the culture receptacle on the horizontal plane for the sideward shear stress stimulation in in vitro culture in an environment similar to an in vivo environment or structure with the interior of the carbon dioxide incubator used in the sterilized environment in which those including the temperature, the humidity and the partial pressures of oxygen, carbon dioxide and nitrogen are controlled.

The biomechanical stimulation loading systems of the invention allow the operations including replacement of the culture medium from outside carbon dioxide incubator 2, thereby permitting continuous culture for a long time. Moreover, these biomechanical stimulation loading systems do not require great power, perform loading of precise weight, and can be made compact.

With these systems, the culture can be cultured in the state closely mimicking the in vivo tissue environment, whereby differentiated and maturated cultures capable of withstanding a mechanical load after transplantation can be produced, and efficient repair and maturation can be performed on the biological tissues.

Performing the in vitro biomechanical load stimulation which could not be obtained in a prior tissue culture art and culturing the culture in the state suitable for transplantation affect growth and differentiation of the culture, thus allowing production of the tissues suitable for transplantation.

Basic medical research using the invention's cell culturing method employing the biomechanical stimulation loading and its system allows the tissues subjected to the in vitro biomechanical load stimulation to form into the differentiated and maturated culture tissues capable of withstanding the mechanical load after transplantation, thus contributing to regeneration of the biological tissues and to transplantation medicine.

The present invention also holds promise of contributing to elucidation of a mechanism of destruction of and damage to the bone, a cartilage, skin and others in that it can apply stimulations extremely similar to respective movements of the living body, such as rising, walking, running, jumping and twisting a knee. Specifically, the invention can convert the vertical weight of the weight loading piston to damaging load weight, can apply vertical impactive stimulation by increasing lowering speed, and can apply the stimulation mimicking the stimulation generated when the knee is twisted by applying strong sideward shear stress while applying the damaging load weight. The present invention can also apply long-duration shear stress by repeating the sideward movement for research on bone wear or the like.

A biomechanical stimulation loading system of the invention can perform mechanical stimulation loadings meeting various conditions, serving as a tissue culture system, is relatively simple and can be reduced in size. This system provides an unconventional advantage in its capability to perform the loadings similar to an in vivo environment, such as vertical mechanical stimulation utilizing gravity and sideward shear stress stimulation via an extracellular matrix. This system can find widespread use as a standard culturing product in many laboratories in the area of tissue regeneration of biomedicine and has the potential for a new industry. If this system is recognized as being useful in culturing culture cells, culture tissues or a construct including the culture cells for a bone or a cartilage and becomes a system of producing the cartilage and others, it can address needs for meniscus regeneration therapy that equal or exceed needs for bone regeneration therapy in number and total ten thousand cases each year only in Japan.

The invention claimed is:

1. A biomechanical stimulation loading system comprising:
    a mechanical stimulation loading device;
    a culture receptacle; and
    a control computer,
    wherein the mechanical stimulation loading device and the culture receptacle are disposed in a carbon dioxide incubator,
    wherein the mechanical stimulation loading device comprises:
    a plurality of weight loading pistons;
    a piston raising and lowering stage supporting the plurality of weight loading pistons to allow vertical movement of the plurality of weight loading pistons within a designated range; and
    a stage lifting and lowering mechanism for vertically moving the piston raising and lowering stage,
    wherein the control computer is configured to drive the stage lifting and lowering mechanism in a specified cycle to effect the vertical movement of the piston raising and lowering stage, and
    wherein the plurality of weight loading pistons weigh on a culture in the culture receptacle when the piston raising and lowering stage is lowered, a piston mounting stage is installed on the piston raising and lowering stage to allow each weight loading piston in the plurality of weight loading pistons to be supported by being inserted into a respective hole of a plurality of holes formed in the piston mounting stage, and the piston raising and lowering stage includes an opening to allow free vertical movement of the plurality of weight loading pistons.

2. The biomechanical stimulation loading system of claim 1, wherein each weight loading piston has an upper end part, and an additional load weight is mounted at the upper end part of each weight loading piston.

3. The biomechanical stimulation loading system of claim 1, wherein each weight loading piston has a lower end part, and a pressure member having a shape suitable for the culture is mounted at the lower end part of each weight loading piston.

4. The biomechanical stimulation loading system of claim 1, wherein the piston mounting stage supporting the plurality of weight loading pistons is movable on a horizontal plane in relation to the piston raising and lowering stage.

5. The biomechanical stimulation loading system of claim 1, wherein the plurality of weight loading pistons are supported by one of the piston raising and lowering stage and a piston mounting stage so as to be prevented from rotating during the vertical movement.

6. The biomechanical stimulation loading system of claim 1, wherein the culture receptacle is detachably mounted to a culture receptacle holding stage of the mechanical stimulation loading device.

7. The biomechanical stimulation loading system of claim 6, further comprising a shear stress loading mechanism for moving or shaking the culture receptacle on a horizontal plane.

8. The biomechanical stimulation loading system of claim 1, wherein the culture receptacle accommodates a fixable receptor having a predetermined shape; and a weight load stimulation part for the culture is defined by a pressure member provided at a lower end part of each weight loading piston and the receptor to be similar to a given shape of one of parts including a knee joint.

9. The biomechanical stimulation loading system of claim 8, wherein the weight load stimulation part defined by the pressure member provided at the lower end part of each weight loading piston and the receptor is provided with a member made of a biocompatible synthetic resin material.

* * * * *